US006583184B1

(12) United States Patent
Duggan

(10) Patent No.: US 6,583,184 B1
(45) Date of Patent: Jun. 24, 2003

(54) COMPOSITIONS HAVING COMFREY AND METHODS FOR REDUCING RETINOID-INDUCED SKIN IRRITATION

(75) Inventor: Michele C. Duggan, Middletown, NY (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 09/722,782

(22) Filed: Nov. 27, 2000

(51) Int. Cl.[7] .................. A01N 25/00; A01N 37/00; A01N 65/00
(52) U.S. Cl. .................. 514/974; 514/558; 514/559; 514/560; 424/725
(58) Field of Search ................. 424/401, 70.1, 424/69, 725; 514/558, 559, 560, 506, 974

(56) References Cited

U.S. PATENT DOCUMENTS

| 4,380,549 A | | 4/1983 | Scott et al. ............... 424/317 |
| 5,140,043 A | | 8/1992 | Darr et al. ............... 514/474 |
| 5,204,105 A | * | 4/1993 | Mausner ............... 424/401 |
| 5,516,793 A | | 5/1996 | Duffy ............... 514/474 |
| 5,578,312 A | | 11/1996 | Parrinello ............... 424/401 |
| 5,690,947 A | | 11/1997 | Habif et al. | |
| 5,703,122 A | | 12/1997 | Duffy ............... 514/474 |
| 5,834,513 A | | 11/1998 | Ptchelintsev et al. ....... 514/561 |
| 5,869,540 A | * | 2/1999 | Smith ............... 424/733 |
| 5,922,335 A | | 7/1999 | Ptchelintsev ............... 424/401 |
| 5,932,229 A | | 8/1999 | Ptchelintsev et al. ....... 424/401 |
| 5,989,572 A | | 11/1999 | Habif et al. | |
| 6,099,849 A | * | 8/2000 | Mansouri ............... 424/401 |
| 6,146,636 A | * | 11/2000 | Breton et al. ............... 424/401 |
| 6,299,889 B1 | | 10/2001 | Cowton et al. | |

FOREIGN PATENT DOCUMENTS

EP 0 906 752 A1 * 4/1999

OTHER PUBLICATIONS

Derwent Abstract of CH688787, Mar. 31, 1998.
Derwent Abstract of RO 112159 6/97.

* cited by examiner

Primary Examiner—Sreeni Padmanabhan
Assistant Examiner—Michael A. Willis
(74) Attorney, Agent, or Firm—Ohlandt, Greeley, Ruggiero & Perle, L.L.P.

(57) ABSTRACT

There is provided a topical composition for treating and/or preventing skin irritation induced by a retinoid. The composition has comfrey. There is also provided a method for treating and/or preventing skin irritation induced by a retinoid. An effective amount of comfrey is applied to the skin.

17 Claims, No Drawings

US 6,583,184 B1

COMPOSITIONS HAVING COMFREY AND METHODS FOR REDUCING RETINOID-INDUCED SKIN IRRITATION

BACKGROUND OF THE INVENTION

1. Field of the Invention

The present invention relates to the use of comfrey. More particularly, the present invention relates to the use of comfrey to ameliorate, prevent, reduce and/or treat irritation caused by topical compositions having a retinoid or a retinoid compound.

2. Description of the Prior Art

Retinoid or retinoid compounds/derivatives (collectively referred to herein as "retinoid" or "retinoids") are vitamin A derivatives. They are used in topical compositions to treat a variety of adverse skin conditions. Such skin conditions include acne, actinic damage, fine lines, wrinkles, warts, psoriasis, dandruff and eczema. Representative compositions having a retinoid are discussed, by way of example, in U.S. Pat. Nos. 3,006,939; 3,060,229; 3,932,665; 4,826,828; and 4,934,114.

However, topical compositions having a retinoid have been limited by way of the amount of retinoid since retinoid contained in the composition has been found to irritate the skin. Such irritation is acute especially when the amount of retinoid in the composition is high. However, some consumers with sensitive skin cannot even tolerate small amounts of retinoid.

The irritation can manifest itself in the form of physical discomfort and/or unaesthetic skin appearance. Such an unaesthetic skin appearance can progress to dermatitis or erythema. The irritation may disturb the user to such an extent that the user will discontinue use of the composition having a retinoid. Alternately, the user may reduce the frequency of use, thereby possibly reducing the effectiveness of the composition for its intended purpose.

Known prior art provides natural and synthetic substances, such as cortisone derivatives, that are useful anti-inflammatory agents in topically applied skin compositions. Such substances are discussed, by way of example, in U.S. Pat. Nos. 5,962,018; 6,008,246; and 6,020,367; and International Application (WO) Nos. 9739726; 9746231; 9848768; and 9850005. However, none of these patents or published applications points out a non-cortisone, anti-inflammatory agent that is particularly suited for reducing skin irritation induced by a retinoid in a topical cosmetic composition.

U.S. Pat. No. 5,578,312 to Parrinello is directed to a skin care system and method To improving the moisture retention in skin, particularly for individuals who are undergoing treatment for life threatening illnesses. As stated in column 2, lines 4.6, et seq., a second embodiment of the moisturizer includes vitamin A and allantoin. Column 4, lines 63 et seq. states that comfrey leaf Contains allantoin. However, this is very specifically directed to a tea solution. Moreover, based upon the specific gravity values of most commercially available Vitamin A materials, all of the exemplified formulas disclose a Vitamin A concentration greater than 1.0 wt. %.

A commercial cosmetic product sold by Avon Products, Inc. under the name Daily Revival contained retinyl palmitate and comfrey. However, the retinyl palmitate was not present in a skin irritating amount, nor was the product used for the treatment or prevention of skin irritation of any kind.

Heretofore, there has been a need for a composition that ameliorates, prevents, reduces and/or treats the irritation induced by a retinoid. It has been found that retinoid-induced irritation has a direct correlation to retinoid efficacy. Thus, simply reducing retinoid content may decrease irritation to the skin, but may also fail to provide an efficacious amount of retinoid. Moreover, consumers with sensitive skin needs may hot tolerate even reduced retinoid content compositions. However, these sensitive skin consumers require, and would benefit from, a retinoid-containing composition that is both tolerated and efficacious. The present composition having comfrey achieves this need.

SUMMARY OF THE INVENTION

It is an object of the present invention to provide a topical composition having comfrey to treat, ameliorate and/or reduce or prevent skin irritation induced by a retinoid.

It is a further object of the present invention to provide a method for treating, that is ameliorating and/or reducing, skin irritation induced by a retinoid.

It is still a further object of the present, invention to provide a method for preventing irritation induced by a retinoid.

These and other objects of the present invention are achieved by a topical composition that has comfrey in an amount effective to prevent and/or treat skin irritation induced by a retinoid.

DETAILED DESCRIPTION OF THE INVENTION

The present invention relates to the surprising recognition that comfrey has a direct effect in mitigating skin irritation induced or caused by the topical use of a retinoid. It has been discovered that comfrey will treat, namely ameliorate and/or reduce, such irritation. It has also been discovered that comfrey will prevent such irritation. The efficacy of the retinoid in a topical composition will not be adversely affected by the addition of comfrey to the composition.

As stated above, retinoids are Vitamin A derivatives. Commonly used retinoids include, but are not limited to, retinal, retinol, retinoic acid, retinyl acetate, retinyl palmitate, retinyl propionate, isotretinoin, synthetic retinoid mimics, and tretinoin. The amount of retinoid in a topical composition varies depending on the condition to be treated or prevented, as well as on the composition and the retinoids themselves. However, for most conditions to be treater or prevented, the amount of retinoid in any composition is about 0.1 percentage by weight (wt %); but no greater than about 1.0 wt %, preferably no greater than about 0.5 wt %, since this amount is associated with some irritation and is always irritating to users with sensitive skin.

The comfrey of the present invention may be derived from any part of the comfrey plant (preferably, *Symphytum officinale*) These parts include the flowers, leaves, roots, seeds and stems. Preferably, the comfrey is extracted from the leaves and roots of the plant. The comfrey extract may be in the form of a liquid or powder. A suitable example of a comfrey extract is available from Cosmetochem under the tradename HERBASOL™. It is an extract obtained from comfrey herbs in approximately 60:40 v:v water in propylene glycol solution. It is about 3.5% to 5.5% active.

Comfrey should be present in the topical composition of the invention in an amount, on an active basis, of at least about 0.005 wt % based on the total weight of the composition to treat retinoid-induced skin irritation. Preferably, comfrey is present in an amount at least about 0.005 wt %. to about 90 wt %, more preferably about 0.01 wt % to about 25 wt %, and most preferably about 0.01 wt. % to about 1.0 wt. % based on the total weight of the composition.

As a guideline, it is preferred that when the retinoid is retinol, the amount of comfrey to retinol ratio is from about 1:5 to about 10:1, more preferably from about 1:4 to about 5:1, or most preferably from about 1:3 to about 5:1.

It should be understood that the effect produced by a retinoid will vary by the type and amount of retinoid used in the topical composition. Accordingly, those skilled in the art will vary the amount to compensate for the various efficacies and concentrations associated with each retinoid, as well as the efficacy of the vehicle used. For example, drying vehicles, such as anhydrous gels, are generally considered to increase the potency/irritation of the retinoid as compared to emollient vehicles, such a oil-in-water creams.

The present invention functions against the irritating effect of a retinoid. As is known in the art, potencies of different retinoids vary. For example, retinoic acid is known to be more potent/irritating than retinol. In contrast, retinyl palmitate is known to be less potent than retinol. For this reason, retinyl palmitate is known to produce less irritation compared to retinol on a weight to weight basis. In fact, when retinyl palmitate is employed in commercial skin care products, there is virtually no irritation associated therewith. As a result, the maximum benefits of the present invention is achieved when the selected retinoid is not retinyl palmitate.

The present composition may take any suitable form such as a cream, an emulsion, a gel, a lotion, a patch, a stick, a towellete, a spray, a mask, an ointment or a solution. The composition preferably has a vehicle to provide bulk and physical form. Suitable vehicles include, but are not limited to, water, alcohols such as ethanol and polyvinyl alcohol, glycerin, propanol, propylene glycol, and mixtures thereof. The present composition may be in a form other than a tea.

The present composition may optionally have one or more of the following ingredients or adjuvants: anesthetics, anti-allergenics, antifungals, antiseptics, chelating agents, colorants, demulcents, pigment altering agents, emollients, emulsifiers, exfoliants, fragrances, humectants, lubricants, moisturizers, preservatives, skin penetration enhancers, stabilizers, sunscreens, surfactants, thickeners, viscosity modifiers, vitamins, or mixtures thereof.

The inclusion of at least one sunscreen is particularly preferred since the retinoid may increase sensitivity of the skin to ultraviolet radiation. Preferably, the sunscreen provides both UVA and UVB protection, or is a combination of sunscreens that provide such protection. The preferred sunscreens are avobenzone, octyl salicylate, oxybenzone, titanium dioxide and cinnamic acid derivatives.

To form a topical composition according to the present invention, comfrey is incorporated into the composition by any suitable method known in the art. Preferably, the composition has both comfrey and a retinoid. The comfrey and retinoid may be admixed, preferably with a vehicle and any other adjuvants or ingredients, to form the topical composition.

When the composition includes comfrey, and no retinoid, the composition may be applied either before or after the retinoid is applied to the skin. Preferably, the topical composition having comfrey is applied either immediately before or immediately after the application of a composition containing the retinoid. More preferably, the topical composition of the present invention includes both comfrey and the retinoid for simultaneous application.

The following is an illustrative, non-limiting example of the present invention.

EXAMPLE

The efficacy of comfrey in reducing skin irritation induced by the topical application of retinol was demonstrated. Patch tests were conducted on 20 subjects, each treated with (1) retinol+vehicle, vehicle only (as controls), and (3) retinol+vehicle+comfrey (present invention).

Compositions were tested by applying twenty-four (24) hour patch applications of each of the above three topical compositions to the forearm skin of each of the subjects. Irritation was induced by applying a first composition of 0.15 wt % retinol in a cosmetic vehicle and covering the applied area with a patch. A second composition containing 2 wt % (0.04 wt. % active) comfrey and 0.15 wt % retinol (in the same cosmetic vehicle) was applied to the skin, which was covered by a patch. In the control composition, only the vehicle was applied and covered by a patch.

Irritation was rated by the Primary Irritation Index (PII) System, a response frequency distribution method known to those in the art. A PII is a visual value depicting the average irritant response of the test panel as a whole. It is calculated by totaling the frequency of each irritation score and dividing the sum by the total number of test subjects. The PII results are set forth in the Table below.

TABLE

| Test | PII |
| --- | --- |
| vehicle only* | 0.20 |
| vehicle + retinol* | 1.23 |
| vehicle + retinol + comfrey | 0.63 |

*not an example of the present invention

As indicated above, the presence of retinol significantly increased the average skin irritation response of the test panel, by over six times as shown by the higher PII observed for vehicle+retinol compared to the vehicle only. The use of comfrey significantly reduced the average retinoid-induced irritation response of the test panel by half as shown by the lower PII observed for vehicle+retinol+comfrey compared to vehicle+retinol.

It should be understood that the foregoing description is only illustrative of the present invention. Various alternatives and modifications can be devised by those skilled in the art without departing from the invention. Accordingly, the present invention is intended to embrace all such alternatives, modifications and variations that fall within the scope of the appended claims.

What is claimed is:

1. A method of treating, reducing, and/or ameliorating skin irritation induced by a retinoid, comprising applying to the skin a topical composition having an amount of comfrey effective to treat, reduce, and/or ameliorate the retinoid-induced skin irritation, wherein the topical composition is free of a cortisone.

2. The method of claim 1, wherein said comfrey is applied in an amount at least about 0.005 wt % of the total weight of the topical composition.

3. The method of claim 1, wherein the comfrey is applied in an amount from about 0.01 wt. % to about 25 wt. % of the total weight of the composition.

4. The method of claim 1, wherein the comfrey is applied in an amount from about 0.01 wt. % to about 1 wt. % of the total weight of the composition.

5. The method of claim 1, wherein the composition further comprises a retinoid in a skin irritation inducing amount.

6. The method of claim 5, wherein the retinoid is retinol.

7. The method of claim 6, wherein the retinol is present in an amount not greater than about 1.0 wt. % of the total weight of the composition.

8. The method of claim 1, wherein the composition is applied to the skin either immediately before or immediately after a second composition containing a retinoid in a skin irritation inducing amount is applied to the skin.

9. The method of claim 5, wherein the retinoid is not retinyl palmitate.

10. The method of claim 8, wherein the retinoid is not retinyl palmitate.

11. The method of claim 1, wherein the comfrey is an extract of comfrey.

12. The method of claim 11, wherein the comfrey extract is comfrey root extract, a comfrey leaf extract, or a mixture thereof.

13. The method of claim 1, wherein the composition is in a form other than a tea solution.

14. The method of claim 5, wherein the weight ratio of comfrey to retinoid is about 1:4 to about 5:1.

15. The method of claim 1, wherein the topical composition has an amount of comfrey effective to treat the retinoid-induced skin irritation.

16. The method of claim 1, wherein the topical composition has an amount of comfrey effective to reduce the retinoid-induced skin irritation.

17. The method of claim 1, wherein the topical composition having an amount of comfrey effective to ameliorate the retinoid-induced skin irritation.

* * * * *